United States Patent
Forster et al.

(10) Patent No.: US 10,255,468 B2
(45) Date of Patent: Apr. 9, 2019

(54) TRANSMISSION RFID TEST SYSTEMS

(71) Applicant: Avery Dennison Retail Information Services, LLC, Westborough, MA (US)

(72) Inventors: Ian J. Forster, Chelmsford (GB); Adrian N. Farr, Dunmow (GB)

(73) Assignee: AVERY DENNISON RETAIL INFORMATION SERVICES, LLC, Mentor, OH (US)

( * ) Notice: Subject to any disclaimer, the term of this patent is extended or adjusted under 35 U.S.C. 154(b) by 210 days.

(21) Appl. No.: 15/337,437

(22) Filed: Oct. 28, 2016

(65) Prior Publication Data
US 2018/0121690 A1 May 3, 2018

(51) Int. Cl.
*G06K 7/10* (2006.01)
*G01N 27/72* (2006.01)

(52) U.S. Cl.
CPC ......... *G06K 7/10465* (2013.01); *G01N 27/72* (2013.01); *G06K 7/10336* (2013.01); *G06K 7/10346* (2013.01); *G06K 7/10356* (2013.01)

(58) Field of Classification Search
CPC ........... G06K 7/10465; G06K 7/10356; G06K 7/10336; G06K 7/10346; G01N 27/72
USPC ....... 324/200, 207.3, 244, 253, 254
See application file for complete search history.

(56) References Cited

U.S. PATENT DOCUMENTS

| | | | | |
|---|---|---|---|---|
| 6,617,972 B2 * | 9/2003 | Takarada | ........... | G08B 21/0484 324/538 |
| 8,779,729 B2 * | 7/2014 | Shiraishi | ............ | G01R 31/3606 320/155 |
| 2006/0000907 A1 | 1/2006 | Forster | | |
| 2006/0217906 A1 * | 9/2006 | Barbara | ................... | G01R 1/36 702/60 |
| 2006/0226983 A1 | 10/2006 | Forster | | |
| 2006/0250245 A1 | 11/2006 | Forster | | |
| 2006/0250246 A1 | 11/2006 | Forster | | |
| 2010/0281854 A1 * | 11/2010 | Huang | ................ | F02D 41/1495 60/276 |
| 2012/0098518 A1 * | 4/2012 | Unagami | ............. | G01R 22/066 324/74 |
| 2012/0182023 A1 * | 7/2012 | Zhang | ................ | G01M 11/3109 324/501 |

OTHER PUBLICATIONS

International Search Report and Written Opinion prepared for PCT/US2017/058717 dated Feb. 12, 2018.

* cited by examiner

*Primary Examiner* — Giovanni Astacio-Oquendo
(74) *Attorney, Agent, or Firm* — Avery Dennison Retail Information Services, LLC

(57) ABSTRACT

An RFID test system is disclosed that establishes a minimum coupling between two ports without an RFID tag present and a higher coupling when the RFID tag is present. Furthermore, this controlled coupling in the presence of an RFID tag is used to read and identify tags. The RFID tag is read when it is in the coupling zone, as it receives maximum power and has the lowest loss path to the receiver. Adjacent tags do not couple efficiently, so they are isolated from the wanted device (i.e., RFID tag). Further, the coupling through the RFID tag can be frequency specific, and the peak frequency can be determined. This peak frequency and also the amount of coupling can give a good indication of a number of aspects of the tag assembly.

20 Claims, 5 Drawing Sheets

TRANSMISSION RFID TEST SYSTEMS

BACKGROUND

The present invention relates generally to radio frequency identification (RFID) test systems and devices. More particularly, the present disclosure relates to an RFID test system that establishes a minimum coupling between two ports without an RFID tag present and a higher coupling when the RFID tag is present.

Radio frequency identification (RFID) devices are well known and are increasingly utilized in a wide variety of applications. However, one challenge associated with RFID devices (e.g., RFID tags, RFID labels, RFID chips, RFID straps, or RFID inlays) is the manufacture and testing of the RFID devices in a high-volume and cost-effective manner.

For example, during or after the manufacturing process, the RFID devices may be tested while located in close proximity to each other (e.g., adjacent RFID devices closely spaced). The RFID devices, as an example, may be manufactured on a common carrier web, with the RFID device (e.g., an RFID inlay) having its antenna mounted on the common carrier web and its integrated circuit mounted to the antenna.

Due to the close proximity of the RFID devices, it may be difficult to establish bi-directional communication with each of the RFID devices during testing. In general, an antenna of the RFID device may be viewed as having a near field region and a far field region. The near field region refers to a reactive near field and a radiating near field, while the far field region refers to a radiating far-field component. Short-range testing of RFID devices generally involves testing within the near field region (e.g., utilizing the near or far-field components), while long-range testing generally involves testing within the far field region.

For short-range testing and long-range testing, typically certain precautions must be taken, when testing one of the RFID devices, to prevent the RFID devices that are in close proximity from also responding or affecting the test results for each RFID device being tested. This results in complicated test procedures or test setups and may lead to operational RFID devices that are tested and erroneously determined to be defective. As a result, there is a need for improved test techniques for RFID devices.

The present invention discloses an RFID test system that establishes a minimum coupling between two ports without an RFID tag present and a higher coupling when the RFID tag is present. Furthermore, this controlled coupling in the presence of an RFID tag is used to read and identify tags. The RFID tag is read when it is in the coupling zone, as it receives maximum power and has the lowest loss path to the receiver. Adjacent tags do not couple efficiently, so they are isolated from the wanted device (i.e., RFID tag). Further, the coupling through the RFID tag can be frequency specific, and the peak frequency can be determined. This peak frequency and also the amount of coupling can give a good indication of a number of aspects of the tag assembly.

SUMMARY

The following presents a simplified summary in order to provide a basic understanding of some aspects of the disclosed innovation. This summary is not an extensive overview, and it is not intended to identify key/critical elements or to delineate the scope thereof. Its sole purpose is to present some concepts in a simplified form as a prelude to the more detailed description that is presented later.

The subject matter disclosed and claimed herein, in one aspect thereof, comprises a radio frequency identification (RFID) test system that establishes a minimum coupling between two ports without an RFID tag present and a higher coupling when the RFID tag is present. Specifically, the RFID test system uses electric or magnetic near field transmit and receive elements (components) that have a minimum coupling due to their geometric relationship. The RFID tag then provides a path for the signal when the tag is present.

Furthermore, this controlled coupling in the presence of an RFID tag is used to read and identify tags. For example, the transmit port is connected to the transmit port on the RFID reader and the receive port is connected to the receive port of the same reader, the RFID tag is read when it is in the coupling zone, as it receives maximum power and has the lowest loss path to the receiver. Adjacent tags do not couple efficiently, so they are isolated from the wanted device (i.e., RFID tag).

In a preferred embodiment, a combination of magnetic and electric field transmit and receive elements that inherently do not couple are used, and the RFID tag provides a conversion between the two field types.

To the accomplishment of the foregoing and related ends, certain illustrative aspects of the disclosed innovation are described herein in connection with the following description and the annexed drawings. These aspects are indicative, however, of but a few of the various ways in which the principles disclosed herein can be employed and is intended to include all such aspects and their equivalents. Other advantages and novel features will become apparent from the following detailed description when considered in conjunction with the drawings.

DETAILED DESCRIPTION

Figure 1A:
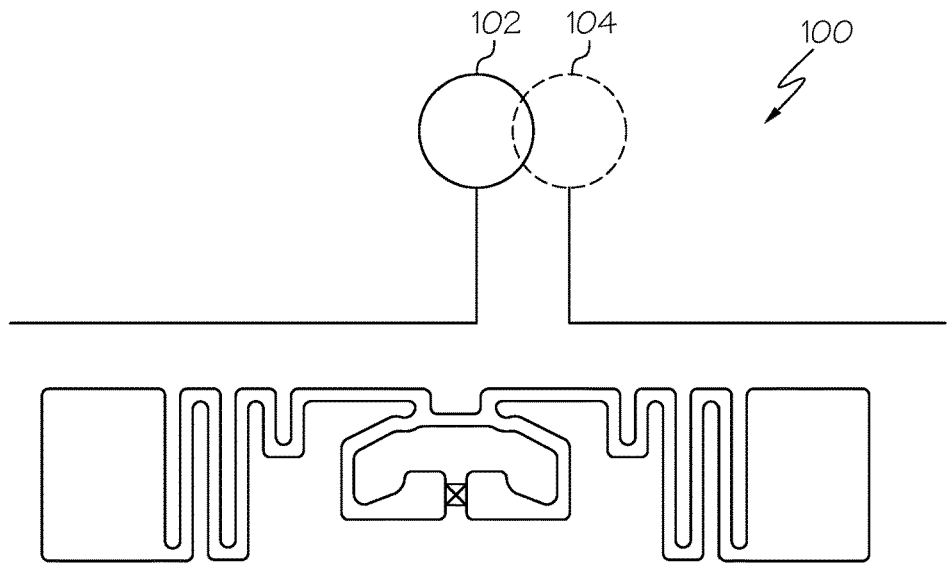
FIG. 1A illustrates a perspective view of the magnetic near field in the magnetic test system in accordance with the disclosed architecture.

The innovation is now described with reference to the drawings, wherein like reference numerals are used to refer to like elements throughout. In the following description, for purposes of explanation, numerous specific details are set forth in order to provide a thorough understanding thereof. It may be evident, however, that the innovation can be practiced without these specific details. In other instances, well-known structures and devices are shown in block diagram form in order to facilitate a description thereof.

Typically RFID devices may be tested during or after the manufacturing process, for example, with a RFID device tester. The RFID device tester may represent a near-field tester, a far-field tester, or some combination of near-field and far-field testers, as discussed further herein. Furthermore, the RFID device tester may be incorporated into a device, such as for example a printer for printing information on RFID devices (e.g., RFID labels) and programming and/or testing RFID devices.

Because RFID devices are in close proximity to each other, it has been determined that the test results for one RFID device will be influenced or affected by other RFID devices nearby (e.g., due to interaction of RFID devices). RFID devices that influence or affect the test results may be adjacent to and/or in the general area of the RFID device being tested, which may depend, for example, upon the application, environment, and type of RFID devices, including inlay pitch (i.e., spacing) and/or antenna fields.

Furthermore, for example, the degree of influence or interaction among RFID devices may depend upon their spacing relative to a wavelength of a test frequency. As an example, RFID devices may be spaced a relatively small fraction of a wavelength from a RFID device being tested, which may result in a relatively low interaction (e.g., a near field effect) with the RFID device being tested. However, the relative interaction may increase for RFID devices that are separated from the RFID device being tested by one-quarter wavelength, one-half wavelength, or other wavelength increments, due to the interactions having specific phase relationships at these distances.

RFID device tester may test RFID devices, for example at a test position currently occupied by a RFID device, by determining its ability to communicate with the RFID device tester at a defined power or voltage level and frequency. Conventional test techniques would apply a certain fixed threshold for every RFID device, with any of RFID devices failing to exceed the fixed threshold considered defective.

Thus, conventional test methods set test thresholds in a static way, which fail to account for the effect of RFID devices adjacent to the RFID device under test (e.g., in a roll format). Consequently, the conventional test methods may result in erroneous test results regarding whether the RFID device is operational (e.g., if the RFID device is good or bad) and lead to reduced quality and/or yields from the manufacturing process.

In contrast, in accordance with one or more embodiments of the present invention, RFID device test techniques are disclosed that apply a variable threshold (e.g., an adaptive threshold) to RFID devices that takes into account the characteristics of nearby RFID devices (e.g., adjacent RFID devices). Consequently, for example, the variable threshold based on adjacent RFID device test results may provide more accurate and reliable test results, which may lead to increases in quality and manufacturing yields.

Furthermore, coupling may represent one or more pairs of couplers to couple via an electric field with the RFID device (e.g., capacitively couple to an antenna of RFID device). Alternatively, or in addition, coupling may represent a coil (e.g., a single-turn coil or a multi-turn coil) to couple via a magnetic field with an RFID device (e.g., inductively couple to the antenna of the RFID device). Thus, coupling includes coupling to an RFID device via an electric field, a magnetic field, or some combination of electric and magnetic fields (electromagnetic field), with the appropriate structure (e.g., parallel plates, single or multi-turn coils, transmission lines, or other types of structures).

A RFID test system is disclosed that establishes a minimum coupling (or null state) between two ports without an RFID tag present and a higher coupling (or controlled coupling) when the RFID tag is present. This null state can be achieved in multiple ways. First, electric or magnetic near field transmit and receive elements are used that have a minimum coupling due to their geometric relationship. Then, the RFID tag, when present, provides a path for the signal. A second method, is using a combination of magnetic and electric field transmit and receive elements that inherently do not couple. Then, when the RFID tag is present, the RFID tag provides a conversion between the two field types.

In either method, once the tag is present, controlled coupling occurs. This controlled coupling in the presence of an RFID tag can be used in a number of ways. First, the coupling through the RFID tag, depending on the chosen mode (i.e., electric or magnetic), can be frequency specific, and the peak frequency can be determined. This peak frequency, and also the amount of coupling (i.e., amplitude), can give a good indication of a number of aspects of the tag assembly.

Second, by connecting the transmit port to the transmit port on an RFID reader, and the receive port to the receive port of the same reader, the tag can be read when it is in the coupling zone, as it receives maximum power and has the lowest loss path to the receiver. Adjacent tags, that is those on either side of the wanted tag when the tags are in a single or multiple lane roll format, do not couple efficiently, so they are isolated from the wanted device. Further, an RFID reader represents any type of conventional source for providing the RF signal to an RFID device.

Third, if a roll of RFID tags are moving through the aperture of the coupler, a detector of the maximum power transfer is able to determine with good precision where the RFID tag is, which acts as a trigger for other systems.

It will be appreciated that where in the descriptions below a particular type of field and antenna is described as transmitting or creating, and another element receiving, the nature of these elements may be swapped over without changing the effectiveness of the test system. Further, where the descriptions below state a particular RFID device, the RFID device comprises at least one of RFID tags, RFID labels, RFID chips, RFID straps, and RFID inlays.

Figure 1B:
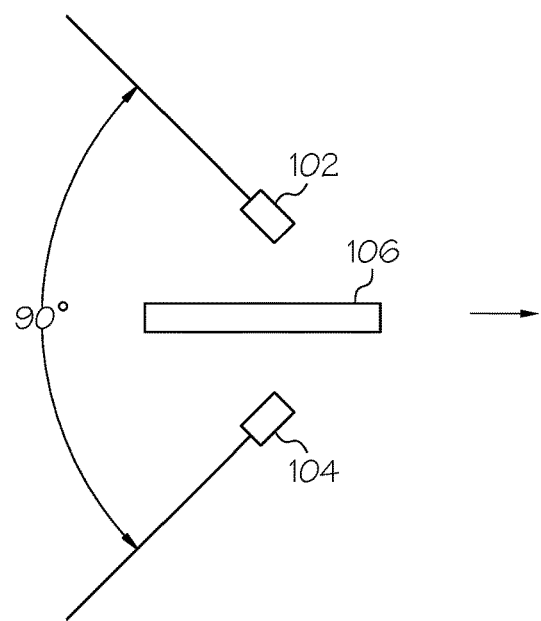
FIG. 1B illustrates a schematic view of the magnetic near field in the magnetic test system in accordance with the disclosed architecture.

Referring initially to the drawings, FIG. 1A AND FIG. 1B illustrate a magnetic near field in the magnetic near field test system 100. The coupling between the transmit (loop 1) 102 and receive (loop 2) 104 is dependent on the inverse cube law for distance but also the cosine of the relative angle between the coils. Thus, without a tag present, the relative angle between loop 1 and loop 2 is 90 degrees, and cosine of that is zero, so the coupling is at a minimum. However, with an RFID tag 106 present which has a frequency specific magnetic coupling response, loop 1 (102) couples to the magnetic element of the RFID tag 106 and induces a current as the angle is less than 90 degrees. For example, if the angle is 45 degrees, the coupling is 0.707 magnitude, and when the relative angle is 0 degrees, there is full coupling. Further, the current flowing in the frequency specific magnetic element of the RFID tag 106 creates its own magnetic field. Accordingly, this magnetic element is approximately at 45 degrees to loop 2 (104), coupling to that with a 0.707 magnitude. In this way, a path at the magnetic operating peak for the RFID tag 106 is created.

Figure 2:
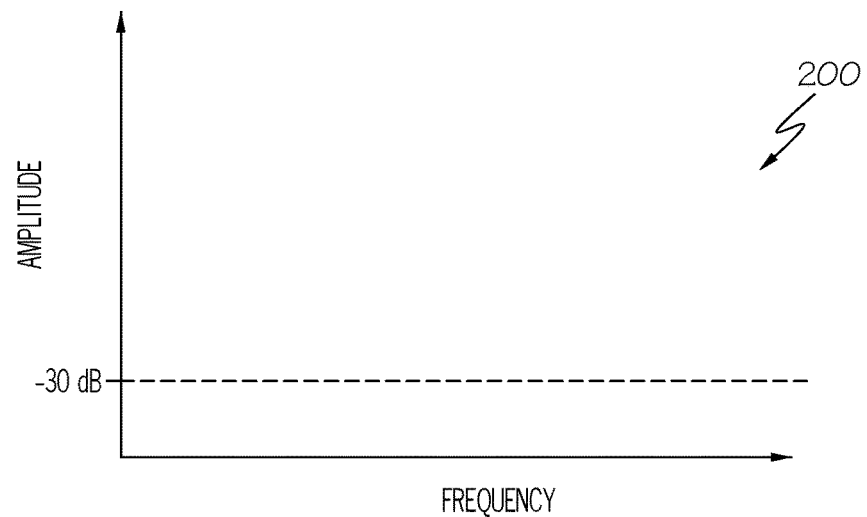
FIG. 2 illustrates a graphical view of the frequency response during the magnetic test system in accordance with the disclosed architecture.
Figure 2:
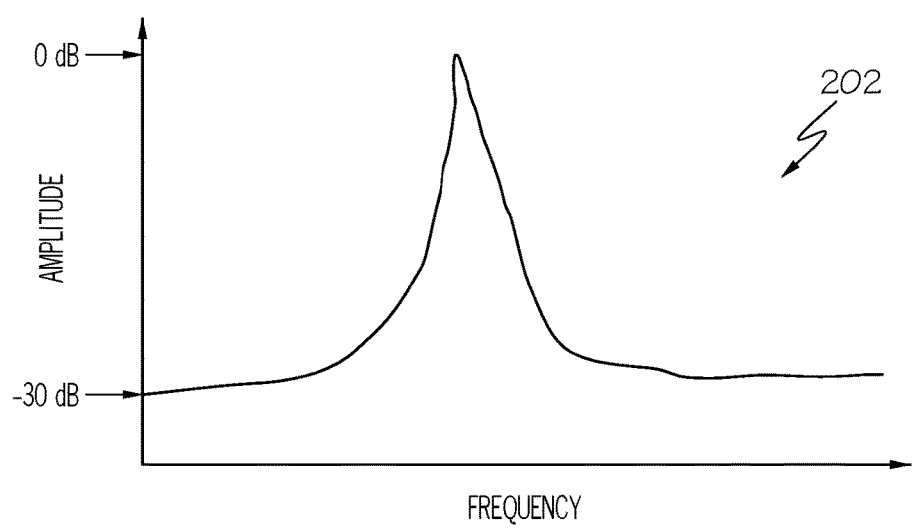

The frequency response is illustrated in FIG. 2, wherein when there is no RFID tag present, there is a null condition 200. In a null condition, the coupling between loop 1 and loop 2 is very low. For example, FIG. 2 shows −30 dB with respect to full coupling 202. Then, when the RFID tag passes between the two loops (loop 1 and loop 2), the path is created and the transmission loss drops to a relative 0 dB at the magnetic resonance point frequency.

Figure 3:
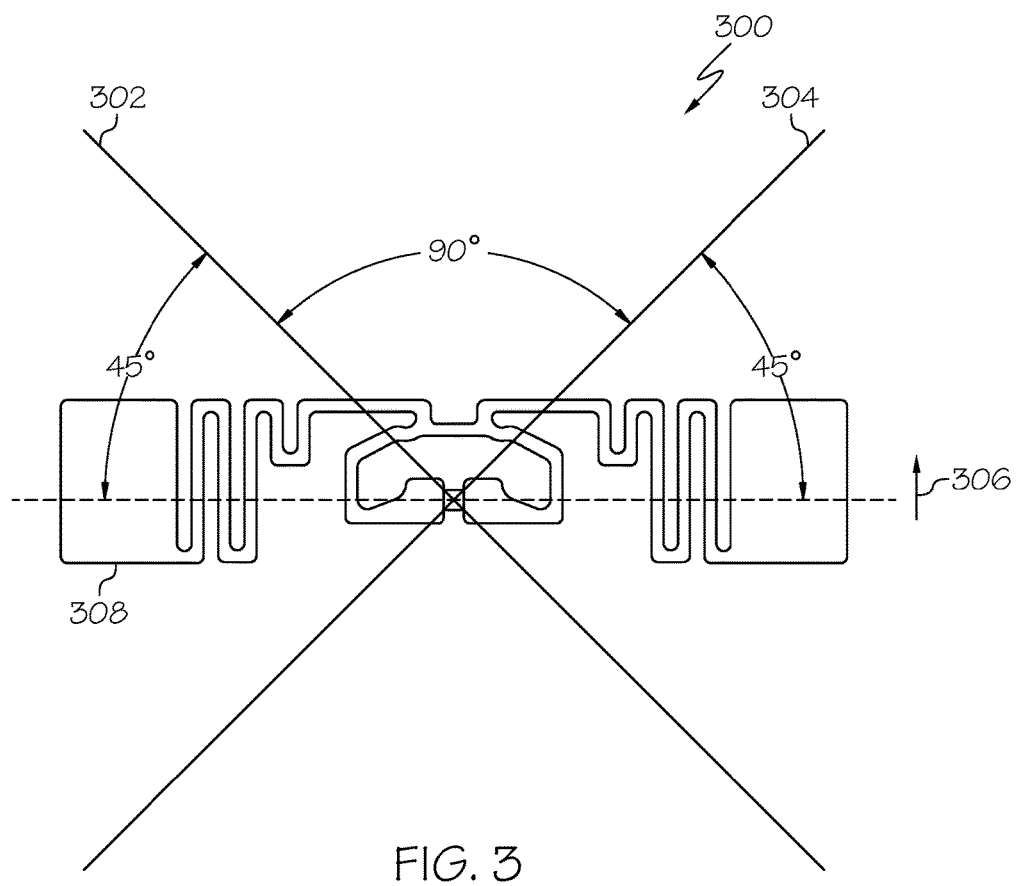
FIG. 3 illustrates a perspective view of the electrical field in the electrical test system in accordance with the disclosed architecture.

FIG. 3 shows an electrical field to electrical field transmission test system 300. In this system, the coupling between dipole 1 (302) and dipole 2 (304) is a minimum when their long directions are at 90 degrees. Then, when a RFID tag 306 is present, the angle to dipole 1 (302) shrinks to less than 90 degrees, so a voltage is induced into the antenna 308. This induced voltage can couple to dipole 2 (304) as it also has an angle to the long direction of the RFID tag 306 of less than 90 degrees (i.e., 45 degrees). The transmission response with and without an RFID tag 306 is as shown in FIG. 2.

Figure 4:
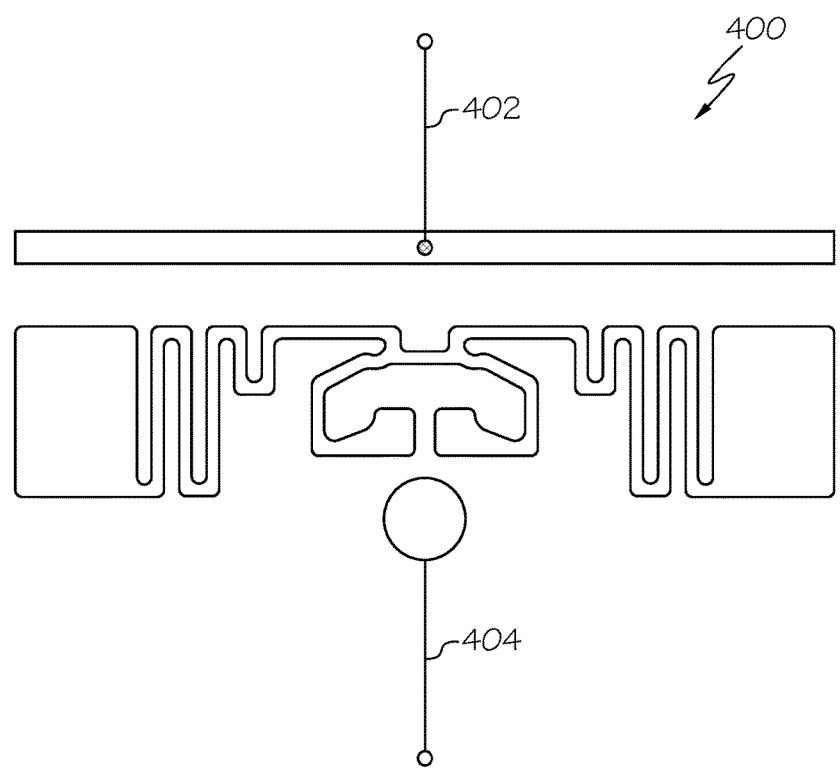
FIG. 4 illustrates a perspective view of an electrical field converted to a magnetic field in a conversion system in accordance with the disclosed architecture.

FIG. 4 shows an electrical field to magnetic field conversion system 400. Short dipole 1 (402) creates a near electric field with minimum magnetic field associated with it. The coupling between dipole 1 (402), which can be considered an electric field emitter, and loop 1 (404) which is a magnetic field receiver is inherently low. Then, when a RFID tag is present the received electric field, in the form of a differential voltage, causes a current to flow. The current flowing generates a magnetic field at the frequency of peak conversion that is detected by loop 1 (404) giving relatively strong coupling.

Figure 5:
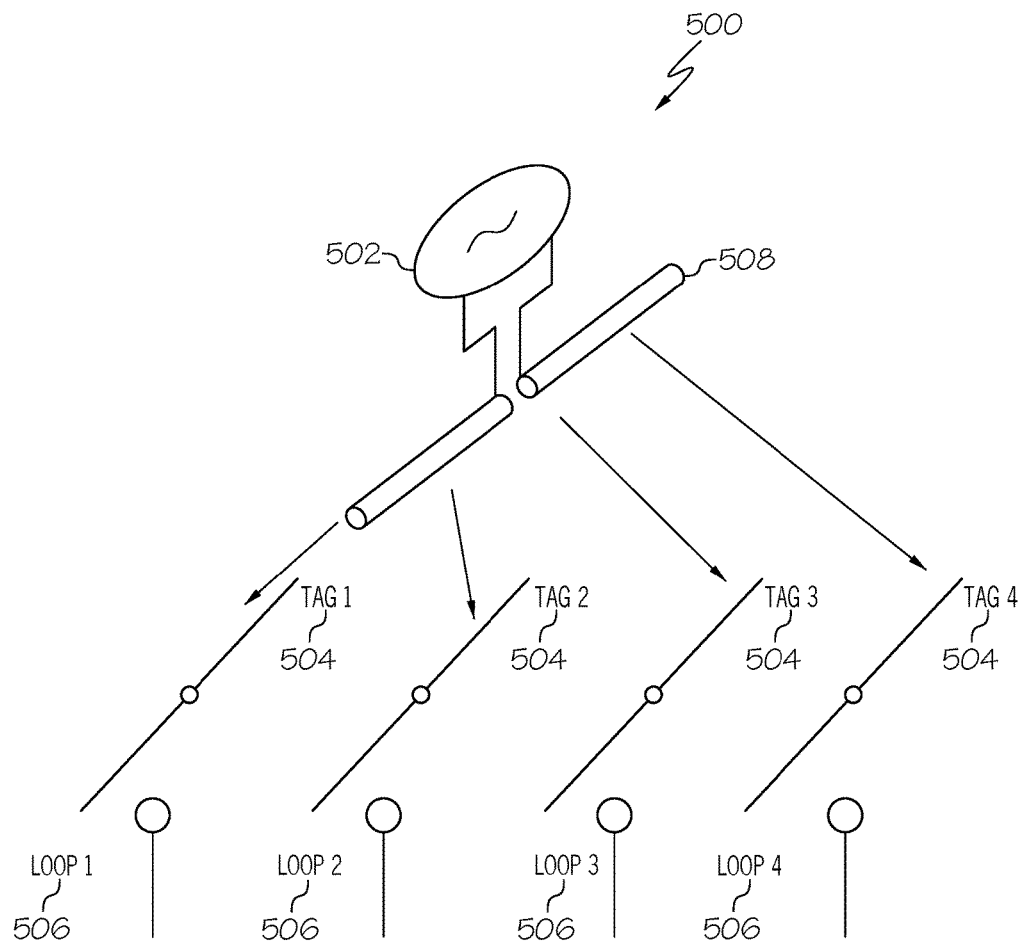
FIG. 5 illustrates a perspective view of an alternative system in accordance with the disclosed architecture.

FIG. 5 shows an alternative system 500. As per the structure shown in FIG. 4, a dipole type antenna is driven by a source 502 such as a swept frequency generator or an RFID reader. However, a number of RFID tags 504 and detecting loops 506 are in the near or radiating near field with respect to the dipole 508, (i.e., tags 1-4 (504) and loops 1-4 (506)). As previously stated, without an RFID tag present, the coupling between dipole 1 (508) and loops 1-4 (506) is a minimum, and with an RFID tag present, the coupling is greatly increased. In the event that the tag peak frequency of coupling is required, the variable frequency source can be swept across a defined band at a certain rate. The time in the sweep when the signal on loops 1-4 (506) reaches a maximum is indicative of the peak coupling frequency of that tag. In this way, the peak coupling frequency of a number of RFID tags can be determined simultaneously, increasing the overall test speed.

The RF signal having a variable field strength profile, in accordance with one or more embodiments of the present invention, may be provided to one or more RFID devices moving through the test region by utilizing short-range techniques (e.g., near field coupling) and/or long-range techniques (e.g., far field transmission utilizing a radiating electromagnetic field). In general, an antenna of the RFID device may be viewed as having a near field region and a far field region. The near field region refers to a reactive near field and a radiating near field, while the far field region refers to a radiating far-field component. Thus, short-range communication generally involves the reactive near field, radiating near field, radiating far field, and/or a direct electrical connection, while long-range communication generally involves the radiating far field.

It should be understood that these various factors for varying the RF field strength are exemplary and may be utilized separately or in any combination, as desired and depending upon the implementation requirements. Furthermore, additional techniques may be utilized alone or in combination with the techniques discussed herein.

The short-range couplers may couple via an electric field with the RFID device (e.g., in a capacitive fashion). Alternatively, or in addition, the short-range couplers may couple via a magnetic field by utilizing a coil (e.g., single-turn coil or multi-turn coil) to couple with RFID device (e.g., in an inductive fashion). Thus, the short-range couplers may couple to the RFID device via an electric field, a magnetic field, or some combination of electric and magnetic fields (electromagnetic field), with the short-range couplers providing the appropriate structure (e.g., parallel plates, single or multi-turn coils, transmission lines, or other types of structures). Thus, the short-range couplers may provide short-range coupling in the near field via electric and/or magnetic fields or by direct connection with the RFID device.

What has been described above includes examples of the claimed subject matter. It is, of course, not possible to describe every conceivable combination of components or methodologies for purposes of describing the claimed subject matter, but one of ordinary skill in the art may recognize that many further combinations and permutations of the claimed subject matter are possible. Accordingly, the claimed subject matter is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A magnetic RFID test system, comprising:
    a first transmit loop; and
    a second receive loop; and
    wherein coupling between the first loop and the second loop is dependent on the inverse cube law for distance but also the cosine of a relative angle between coils; and
    wherein the relative angle between the first loop and the second loop is 90 degrees so coupling is at a minimum.

2. The magnetic RFID test system of claim 1, further comprising an RFID tag with a frequency specific magnetic element.

3. The magnetic RFID test system of claim 2, wherein a signal level of the RFID tag changes as the RFID tag moves through a test region by varying a distance between the first and the second loops and the RFID tag.

4. The magnetic RFID test system of claim 3, wherein when the RFID tag is present, the angle becomes less than 90 degrees between the first loop and the RFID tag, and the first loop couples to the magnetic element of the RFID tag and induces a current.

5. The magnetic RFID test system of claim 4, wherein when the relative angle between the first loop and the RFID tag is 45 degrees, the coupling is 0.707 magnitude.

6. The magnetic RFID test system of claim 4, wherein when the relative angle between the first loop and the RFID tag is 0 degrees, there is full coupling.

7. The magnetic RFID test system of claim 4, wherein current flowing in the frequency specific magnetic element of the RFID tag creates a magnetic field.

8. The magnetic RFID test system of claim 7, wherein the magnetic element is approximately at 45 degrees to the second loop, and is coupled with a 0.707 magnitude to create a path for an RFID tag at a magnetic operating peak.

9. The magnetic RFID test system of claim 8, wherein if no RFID tag is present, a null condition is created.

10. The magnetic RFID test system of claim 9, wherein in the null condition, coupling between the first loop and the second loop is approximately 30 dB with respect to full coupling.

11. The magnetic RFID test system of claim 8, wherein when an RFID tag passes between the first loop and the second loop, a path is created and a transmission loss drops to approximately 0 dB at a magnetic resonance point frequency.

12. An electrical RFID test system, comprising:
a first dipole; and
a second dipole; and
wherein long directions between the first dipole and the second dipole is 90 degrees so coupling is at a minimum.

13. The electrical RFID test system of claim 12, wherein when an RFID tag is present, an angle between the RFID tag to the first dipole shrinks to less than 90 degrees which induces voltage into an antenna.

14. The electrical RFID test system of claim 13, wherein the induced voltage can couple to the second dipole as an angle between the second dipole to a long direction of the RFID tag is less than 90 degrees.

15. An electrical to magnetic RFID test conversion system, comprising:
a first short dipole which is an electric field emitter that creates a near electric field with minimum magnetic field associated with it; and
a first receive loop which is a magnetic field receiver; and
wherein coupling between the first dipole and the first loop is low.

16. The electrical to magnetic RFID test conversion system of claim 15, wherein when an RFID tag is present, received electric field in a form of a differential voltage causes a current to flow.

17. The electrical to magnetic RFID test conversion system of claim 16, wherein the current flowing generates a magnetic field at a frequency of peak conversion that is detected by the first loop which results in strong coupling.

18. The electrical to magnetic RFID test conversion system of claim 17, wherein a dipole type antenna is driven by a variable frequency generator.

19. The electrical to magnetic RFID test conversion system of claim 17, wherein a dipole type antenna is driven by an RFID reader.

20. The electrical to magnetic RFID test conversion system of claim 17, wherein a plurality of tags and detecting loops are positioned in a near field.

\* \* \* \* \*